United States Patent [19]

Ranken et al.

[11] Patent Number: 4,670,597

[45] Date of Patent: * Jun. 2, 1987

[54] PROCESS FOR PREPARING (HYDROCARBYLTHIO) AROMATIC AMINES

[75] Inventors: Paul F. Ranken; Robert L. Davis, both of Baton Rouge, La.

[73] Assignee: Ethyl Corporation, Richmond, Va.

[*] Notice: The portion of the term of this patent subsequent to Jun. 10, 2003 has been disclaimed.

[21] Appl. No.: 796,264

[22] Filed: Nov. 8, 1985

[51] Int. Cl.$^4$ .............................................. C07C 149/42
[52] U.S. Cl. .................................. 564/440; 564/307; 564/335; 564/427; 564/428; 564/430; 546/290; 548/337; 548/484; 548/541
[58] Field of Search ............... 564/440, 307, 335, 427, 564/428, 430; 546/290; 548/337, 484, 541

[56] References Cited

U.S. PATENT DOCUMENTS 4,594,453  6/1986  Ranken et al. ...................... 564/440

Primary Examiner—Charles F. Warren
Assistant Examiner—John A. Sopp
Attorney, Agent, or Firm—Donald L. Johnson; John F. Sieberth; Patricia J. Hogan

[57] ABSTRACT

(Hydrocarbylthio)aromatic amines are prepared by reacting an aromatic monoamine, such as an aminobenzene, with a hydrocarbyl disulfide, such as an alkyl disulfide, in the presence of hydrogen iodide, ammonium iodide, or cuprous iodide.

8 Claims, No Drawings

PROCESS FOR PREPARING (HYDROCARBYLTHIO) AROMATIC AMINES

FIELD OF INVENTION

This invention relates to (hydrocarbylthio)aromatic amines and more particularly to a process for preparing them.

BACKGROUND

As disclosed in copending application Ser. No. 619,675 (Ranken et al.), filed June 11, 1984, now U.S. Pat. No. 4,594,453, it is known that various (hydrocarbylthio)aromatic amines are useful as intermediates in the preparation of biologically-active materials, polyurethanes, etc.; and they can be prepared by reacting an aromatic amine with a hydrocarbyl disulfide in the presence of a catalytic amount of a Lewis acid. The preferred catalysts of Ranken et al. are metal halides, such as aluminum chloride, boron trifluoride, boron trichloride, ferric chloride, and zinc chloride.

It has been found that the preferred catalysts identified by Ranken et al. sometimes have the disadvantages of effecting the desired hydrocarbylthiations at too slow a rate to be completely satisfactory and of sometimes providing too low a yield of product.

SUMMARY OF INVENTION

An object of this invention is to provide a novel process for preparing (hydrocarbylthio)aromatic amines.

Another object is to provide such a process wherein the products are prepared by the hydrocarbylthiation of aromatic monoamines in the presence of Lewis acid catalysts.

A further object is to provide such a process wherein the reaction rates and/or product yields are improved.

These and other objects are attained by reacting an aromatic monoamine with a hydrocarbyl disulfide in the presence of a catalytic amount of a Lewis acid selected from hydrogen iodide, ammonium iodide, and cuprous iodide.

DETAILED DESCRIPTION

As defined in this application, aromatic monoamines are aromatic compounds which (1) contain a single amino group per aromatic ring, regardless of whether that amino group is a part of a heterocyclic ring or a substituent on a carbocyclic ring or heterocyclic ring, (2) optionally contain another amino group in or on any other ring that is a part of the compound, (3) bear no additional substituents other than hydrocarbyl or hydrocarbylthio substituents, and (4) are free of substituents in the positions ortho to the required amino group and any other positions to be substituted by hydrocarbylthio groups. Such compounds that are utilizable in the practice of the invention include:

(1) compounds having an amino group attached to a carbocyclic or heterocyclic ring of an aromatic compound containing one or more simple and/or fused rings, such as benzene, naphthalene, anthracene, pyrrole, pyridine, indole, etc., rings and (2) reactive heterocyclic amines, such as pyrrole, indole, imidazole, etc.

The compounds may bear no substituents other than the required amino group, or they may bear hydrocarbyl or hydrocarbylthio substituents, such as alkyl, alkylthio, aryl, arylthio, alkaryl, or aralkyl groups, generally such groups containing about 1–10 carbons, on any positions other than ortho positions and any other positions to be substituted by hydrocarbylthio groups. Also, as indicated above, they may bear an additional amino substituent on a ring different from the ring bearing the required amino substituent. In the case of coupled aromatic rings, the rings may be directly attached to one another or may be coupled through a bridge such as an oxygen, sulfur, sulfoxide, sulfone, alkyl, or other hydrocarbon link.

Useful aromatic amines include, e.g., 4,4'-methylenedianiline, 4-aminobiphenyl, 1,3-dimethylpyrrole, 1-methylpyrrole, 7-methylindole, aminobenzenes such as aniline, 4-butylaniline, 4-methylaniline, 3-methylaniline, 4-(phenylthio)aniline, N-methylaniline, etc.

Hydrocarbyl disulfides which may be reacted with the aromatic amines include saturated and unsaturated aliphatic, cycloaliphatic, and aromatic disulfides in which the hydrocarbyl groups optionally bear inert, such as chloro, substituents. Exemplary of such compounds are methyl, ethyl, propyl, n-butyl, sec-butyl, t-butyl, 2-chloropentyl, cyclopentyl, cyclohexyl, phenyl, benzyl, p-tolyl, and p-chlorophenyl disulfides, etc. This component of the reaction mixture is generally employed in at least the stoichiometric amount required to yield the desired (hydrocarbylthio)aromatic amine, i.e., at least an equimolar amount being used when a mono(hydrocarbylthio)aromatic amine is desired, at least two molar equivalents being utilized when a di(hydrocarbylthio)aromatic amine is desired, etc.

The reaction of the aromatic amine with the hydrocarbyl disulfide is generally conducted at a temperature in the range of about 20°–300° C., preferably about 100°–200° C., and at a pressure of atmospheric up to about 1000 psi; and, as mentioned above, it is conducted in the presence of a catalytic amount of hydrogen iodide (commonly employed as hydriodic acid), ammonium iodide, or cuprous iodide. The catalyst may be employed in any catalytic amount, but generally in a catalyst/aromatic amine mol ratio of about 0.01–0.5/1, preferably about 0.01–0.2/1.

In conducting the process of the invention, it is frequently preferred to (1) heat a mixture of the catalyst and aromatic amine at a suitable temperature, usually a temperature higher than the boiling point of the disulfide to be added, e.g., about 100°–150° C., until all of the catalyst has reacted and then (2) heat the reaction mixture at reflux temperature after the disulfide has been added to effect a hydrocarbylthiation process while removing evolved hydrocarbyl thiol by-product from the reaction vessel. However, it is also satisfactory to conduct the process by simply mixing the catalyst and reactants together and heating them to the reflux temperature. An inert solvent may be employed if desired but is unnecessary.

The process of the invention, like the process of Ranken et al., results in the formation of (hydrocarbylthio)aromatic amines which are useful as intermediates in the preparation of biologically-active materials, polyurethanes, etc. It is particularly advantageous in that it is characterized by higher reaction rates and/or higher yields than are obtained in the hydrocarbylthiation of the present aromatic monoamines when the preferred catalysts of Ranken et al. are employed.

The following examples are given to illustrate the invention and are not intended as a limitation thereof.

COMPARATIVE EXAMPLE

A suitable reaction vessel was charged with one molar proportion of aniline and 0.067 molar proportion of aluminum chloride. After the reaction mixture had been stirred in a nitrogen atmosphere at 150° C. for 30 minutes and cooled to 100° C., one molar proportion of methyl disulfide was added. The reaction mixture was then stirred and heated at an initial reflux temperature of 130° C. to a final temperature of 170° C. in 25 hours to provide a crude reaction product which was cooled, worked up, and analyzed by gas chromatography (GC), using n-undecane as an internal standard. The analysis showed that the reaction mixture contained 14 wt% methyl disulfide, 19 wt% aniline, 18 wt% 2-(methylthio)aniline, 33wt% 4-(methylthio)aniline, and 7 wt% 2,4-di(methylthio)aniline.

EXAMPLE I

The Comparative Example was essentially repeated except that the aluminum chloride was replaced with cuprous iodide, the final reflux temperature was 180° C., and the reflux time required was only 20 hours instead of 25 hours. The reaction resulted in the formation of a reaction mixture containing 9 wt% methyl disulfide, 17 wt% aniline, 26 wt% 2-(methylthio)aniline, 26 wt% 4-(methyhlthio)aniline, and 11 wt%, 2,4-di(methylthio)aniline.

EXAMPLE II

A suitable reaction vessel was charged with one molar proportion of aniline and 0.067 molar proportion of ammonium iodide, followed by one molar proportion of methyl disulfide. The reaction mixture was then stirred and heated at an initial reflux temperature of 127° C. to a final temperature of 175° C. in 11 hours. After being cooled and worked up, the reaction mixture was subjected to GC analysis as in the previous examples and found to contain 10 wt% methyl disulfide, 17 wt% aniline, 20 wt% 2-(methylthio)aniline, 27 wt% 4-(methylthio)aniline, and 13 wt% 2,4-di(methylthio)aniline.

EXAMPLE III

Part A

A suitable reaction vessel was charged with one molar proportion of aniline, 1.1 molar proportions of methyl disulfide, and 0.067 molar proportion of 57% hydriodic acid. After the reaction mixture had been heated in a nitrogen atmosphere, and water and methyl disulfide had been collected by distillation to a pot temperature of 134° C., the mixture was stirred and heated at reflux to a final temperature of 180° C. in 3.5 hours to provide a crude reaction product which was cooled, worked up, and analyzed by GC. The analysis showed that the reaction mixture contained 6 wt% methyl disulfide, 31 wt% aniline, 20.5 wt% 2-(methylthio)aniline, 27.4 wt% 4-(methylthio)aniline, and 8 wt% 2,4di(methylthio)aniline.

Part B

An additional 0.445 molar proportion of methyl disulfide was added to the final reaction mixture of Part A, and the mixture was reheated to 180° C. over a period of two hours. Analysis of the product mixture as in Part A showed 8 wt% methyl disulfide, 13 wt% aniline, 23 wt% 2-(methylthio)aniline, 23 wt% 4-(methylthio)aniline, and 23 wt% 2,4-di(methylthio)aniline.

It is obvious that many variations may be made in the products and processes set forth above without departing from the spirit and scope of this invention.

What is claimed is:

1. In a process for reacting an aromatic monoamine with a hydrocarbyl disulfide in the presence of a catalytic amount of a Lewis acid to form a (hydrocarbylthio)aromatic amine, the improvement which comprises conducting the reaction in the presence of hydrogen iodide, ammonium iodide, or cuprous iodide as the Lewis acid.

2. The process of claim 1 wherein the aromatic amine is an aminobenzene.

3. The process of claim 2 wherein the aminobenzene is aniline.

4. The process of claim 1 wherein the hydrocarbyl disulfide is an alkyl disulfide.

5. The process of claim 4 wherein the alkyl disulfide is methyl disulfide.

6. The process of claim 1 wherein the Lewis acid is hydrogen iodide.

7. The process of claim 1 wherein the Lewis acid is ammonium iodide.

8. The process of claim 1 wherein the Lewis acid is cuprous iodide.

* * * * *